United States Patent [19]

Riemen et al.

[11] Patent Number: 5,019,647

[45] Date of Patent: May 28, 1991

[54] GASTRIN RELEASING PEPTIDE ANTAGONIST

[75] Inventors: Mark W. Riemen, Doylestown; Allen I. Oliff, Gwynedd Valley; Walfred S. Saari, Lansdale, all of Pa.; David C. Heimbrook, Ringoes, N.J.

[73] Assignee: Merck & Co., Inc., Rahway, N.J.

[21] Appl. No.: 197,872

[22] Filed: May 24, 1988

[51] Int. Cl.$^5$ .......................... C07K 7/06; C07K 7/30; A61K 37/43
[52] U.S. Cl. .................................. 530/329; 530/309; 530/345
[58] Field of Search ...................... 530/329, 309, 345; 514/17, 16

[56] References Cited

U.S. PATENT DOCUMENTS 4,435,385  3/1984  Bauer et al. ........................ 424/177

FOREIGN PATENT DOCUMENTS 0188947  7/1986  European Pat. Off. .

OTHER PUBLICATIONS

Jensen et al. (1984), Nature 309:61-63.
Marki et al. (1981), J. Am. Chem. Soc. 103:3178-85.
Thaisrivongs et al. (1989), J. Hypertension 1(suppl 2):S21-S23.

*Primary Examiner*—Jeffrey E. Russel
*Assistant Examiner*—Kay Kim
*Attorney, Agent, or Firm*—Frank P. Grassler; Donald J. Perrella; Hesna J. Pfeiffer

[57] ABSTRACT

Small cell lung carcinoma cells (SCLC) contain gastrin releasing peptide (GRP) receptors. The response of the cells to GRP is rapid growth. We have found a group of peptide derivatives that act as GRP antagonists by blocking the binding of GRP to its receptor thereby inhibiting the growth of cells that are sensitive to the growth promoting activity of GRP.

10 Claims, No Drawings

GASTRIN RELEASING PEPTIDE ANTAGONIST

BACKGROUND OF THE INVENTION

Gastrin releasing peptide (GRP), a 27-amino acid hormone, stimulates the growth of small cell lung carcinoma (SCLC) cells in cell culture. Antibodies directed against GRP block the growth of SCLC in nude mice.

DISCLOSURE STATEMENT

Broccardo et al., Br. J. Pharmac. 55:221–227 (1975) compare the pharmacological activity of two (1975) natural bombesin-like peptides and 25 related synthetic peptides to that of bombesin.

Marki et al., Peptides 2, Suppl. 2:169–177 (1981) disclose structure activity relationship of 26 peptide analogs of bombesin and GRP. The minimal essential residues required for full potency of bombesin like effects is represented by an acetylated C-terminal 8-peptide fragment wherein position 7 can be substituted by alanine, histidine, glutamine or D-glutamine. Modification of the tryptophan [8] and histidine [12] residues by alanine abolished the biological potency of these peptides. A blocked N-terminus is necessary for maximum response.

Moody et al., Peptides 4 (5):683–686 (1983) disclose the presence of high concentrations of bombesin-like peptides and receptors in small cell lung cancer (SCLC) and suggest that bombesin may function as an important regulatory agent in human SCLC.

Jensen et al., Nature 309:61–63 (3 May 1984) disclose that a substance P analog is also a bombesin receptor antagonist.

Weber et al., J. Clin. Invest. 75:306–309 (1985) disclose that the mitogenicity of gastrin releasing peptide (GRP) resides in its carboxy terminal fragment, designated GRP 14–27, which is partly homologous to bombesin. The authors speculate that GRP or a closely related small peptide may be acting as an autocrine growth factor for SCLC.

Cuttitta et al., Nature, 316:823–826 (29 Aug. 1985) disclose that a monoclonal antibody to bombesin blocks the binding of the hormone to cellular receptors and inhibits the clonal growth of SCLC in vitro and the growth of SCLC xenografts in vivo demonstrating that bombesin-like peptides can function as autocrine growth factors for human SCLC.

Corps et al., Biochem. J. 231:781–784 (1985) disclose that an analog of substance P inhibits the stimulation of DNA synthesis induced in Swiss 3T3 cells by bombesin.

Bepler et al., Cancer Research 47:2371–2375 (1 May 1987) disclose that the undecapeptide physalaemin inhibits the clonal and mass culture growth of SCLC cell lines at picomolar concentrations.

Heinz-Erian et al., Am. J. Physiol. 252: G439–G442 (1987) disclosed that [D-Phe[12]] analogs of bombesin are the only bombesin receptor antagonists identified to date that interact only with the bombesin receptor.

OBJECTS OF THE INVENTION

It is an object of the present invention to provide peptide derivatives that act as antagonists of GRP. A further object is to provide a method of treating SCLC by administering a peptide derivative of the present invention. Another object is to provide methods for preparing these peptide derivatives. These and other objects of the present invention will be apparent from the following description.

SUMMARY OF THE INVENTION

A series of peptide derivatives have been found which are GRP antagonists and which suppress GRP-stimulated mitogenesis in Swiss 3T3 cells.

The peptide derivatives of the present invention have the following formula:

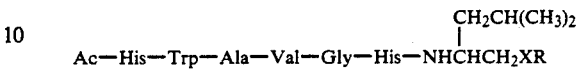

wherein Ac is acetyl, X is O, S or N—H, R is H or an alkyl radical of 1 to 6 carbon atoms, or an alkyl radical of 1 to 6 carbon atoms containing an aromatic radical in which optically active carbon atoms are in the S configuration, wherein both the alkyl and aromatic radicals are optionally substituted with alkyl of from 1 to 3 carbon atoms, hydroxy, alkoxy of from 1 to 3 carbon atoms, halogen, trifluoromethyl, and wherein any one optically active amino acid may be substituted by its D-isomer, and glycine may be substituted by Ala or D-Ala.

DETAILED DESCRIPTION OF THE INVENTION

The activity of the peptide derivatives of the present invention as GRP antagonists was determined in competitive binding assays with a radio-active GRP derivative. Swiss 3T3 fibroblasts were used in these tests as the source of GRP receptor. Because these cells respond to GRP binding with a rapid increase in DNA synthesis, compounds that bind to the GRP receptor can also be tested for their ability to stimulate DNA synthesis. New DNA synthesis is one of the early steps in cell division and is widely accepted as a measure of mitogenicity or cell growth. Compounds which bind to the receptor and do not stimulate growth are then tested for their ability to block GRP stimulated DNA synthesis. Compounds which block DNA synthesis are mitogenic antagonists. The efficacy of these antagonists against the GRP receptor on SCLC was demonstrated by measuring inhibition of GRP dependent calcium release in these cells.

The peptidyl moiety of the peptide derivatives present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980. The teachings of these works are hereby incorporated by reference.

The compounds of the present invention wherein X is oxygen are obtained by reacting approximately equimolar amounts of an alkali metal salt of leucinol of formula I wherein M is, e.g., Na+, Li+ or K+, and of an iodide of formula RI, wherein R has the same meaning as stated above, at temperatures of from about 20° C. to about 65° C. for from about 1 hour to about 24 hours in a dipolar aprotic solvent such as tetrahydrofuran (THF), dimethylformamide (DMF) or dimethylsulfoxide (DMSO).

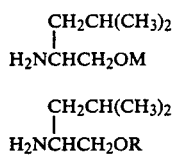

The resulting leucinol or leucinol ether of formula II then is reacted with approximately an equimolar quantity of di-BOC-histidine in the presence of approximately an equimolar quantity of isobutyloxy-carbonyl chloride, and approximately an equimolar quantity of N-methylmorpholine in ethyl acetate. The reaction takes place at temperatures of from about 0° C. to about 60° C. for from about 1 hour to about 24 hours to yield the corresponding 1-alkoxy-4-methyl-2-pentyl-amide of di-BOC-histidine of formula III.

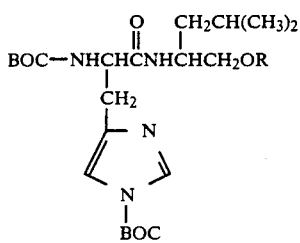

This ether derivative is then deprotected under the usual acidic conditions and reacted with an acetylated pentapeptide of the formula Ac-His-Trp-Ala-Val-Gly or an analog wherein any one optically active amino acid optionally is substituted by its D isomer, and glycine optionally is substituted by Ala or D-Ala, to yield the compound of formula IV or an analog wherein any one optically active amino acid optionally is substituted by its D-isomer, and glycine optionally is substituted by Ala or D-Ala.

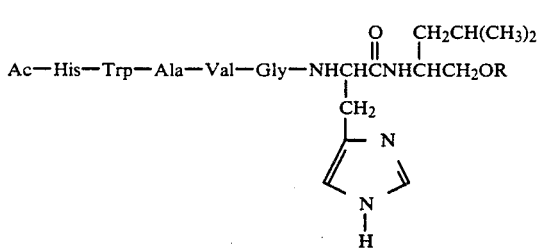

The compounds of the present invention wherein X is sulfur are obtained by the same methods used to prepare the oxygen derivatives except that the starting material is 2-amino-4-methyl-1-pentane thiol.

The compounds of the present invention wherein X is N—H are obtained by a similar procedure in which the NH of the intermediates are protected as the carbobenzyloxy derivative. For example, N-R-N-(2-amino-4-methylpentyl) benzylcarbamate is reacted with approximately an equimolar quantity of di-BOC-histidine in the presence of approximately an equimolar quantity of isobutyloxy-carbonyl chloride, and approximately an equimolar quantity of N-methylmorpholine in ethyl acetate. The reaction takes place at temperatures of from about 0° C. to about 60° C. for from about 1 hour to about 24 hours to yield the corresponding amide of di-BOC-histidine of formula V.

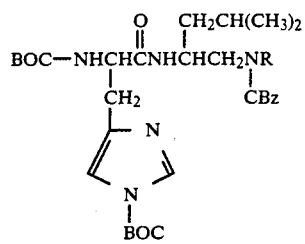

This derivative is then deprotected under the usual acidic conditions and reacted with an acetylated pentapeptide of the formula Ac-His-Trp-Ala-Val-Gly or an analog wherein any one optically active amino acid optionally is substituted by its D-isomer, and glycine optionally is substituted by Ala or D-Ala, to yield the compound of formula VI or an analog, wherein any one optically active amino acid optionally is substituted by its D-isomer, and glycine optionally is substituted by Ala or D-Ala. The benzyloxycarbonyl protective group of the compound of formula VI then is removed under the usual reductive conditions to give the compounds of the present invention where X+NH.

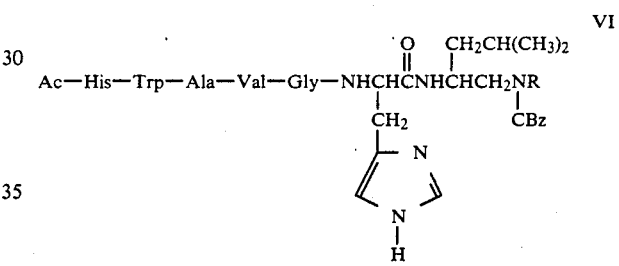

Known peptide antagonists of GRP are based on the structure of bombesin, a GRP analog containing 14 amino acids, or substance P, which contains 11 amino acids. The size of these antagonists are such that pharmacokinetic problems may be encountered. In addition, antagonists based on substance P show cross-reactivity with the substance P receptor.

Current chemotherapeutic agents for the treatment of SCLC are poorly effective. The treatment of SCLC by inhibiting the binding of GRP to its receptor offers advantages over conventional chemotherapy. First, use of a peptide derivative as an antagonist is intended to avoid the gross toxic side affects of conventional chemotherapy. In addition, receptor antagonists do not need to enter the cell to be effective.

The peptide derivatives of the present invention are effective in inhibiting the growth of cells that are sensitive to the growth promoting activity of GRP.

The following procedures were employed in determining the activity of the peptide derivatives of the present invention.

Procedure A

Binding Inhibition Studies

Swiss 3T3 cells, obtained from Dr. K. Brown (Institute of Animal Physiology, Cambridge, U.K.), were grown to confluency in Costar 12 well plates containing DMEM (Gibco) supplemented with 10% fetal bovine serum, 2 mM glutamine and 1% penicillin-streptomycin. The cells were washed twice with binding buffer [1:1 DMEM: Waymouths MB752/1 medium, plus 1 mg/ml BSA (Fraction V, Calbiochem)]. The antagonist was dissolved in 10 mM HCl, and diluted to the appropriate concentration in binding buffer. The antagonist was then added to the cells, followed by [3H-Phe$^{15}$] GRP15-27 at a final concentration of 3 nM. After 60 minutes incubation at 15° C., the supernatant liquid was removed and the cell monolayer rinsed four times with washing buffer (150 mM NaCl, 20 mM Na$_2$HPO$_4$, 5mM KCl, 1.8 mM KH$_2$PO$_4$, 1 mg/ml BSA). The cells were then lysed with 1 ml/well of lysis buffer (1% Triton X-100, 0.1% BSA), and the solution was aspirated into scintillation vials for counting. Each data point was collected in triplicate.

Procedure B

Mitogenic Stimulation

Swiss 3T3 cells were grown in monolayer culture in 24-well plates (Costar) in serum-free DMEM for 48 hours, at which time the GRP or GRP homologue and 23 nM $^3$H-thymidine were added. After an additional 48 hours, the cell monolayer was washed twice with PBS, and the cells were then removed with 1 ml 10×trypsin containing 5 mM EDTA. The cells were harvested with a Skatron filter apparatus, and the filters counted in a scintillation counter.

Procedure C

Mitogenesis Inhibition

Swiss 3T3 cells were grown in monolayer culture in 24 -well plates (Costar) in serum-free DMEM for 48 hours, at which time the GRP or a GRP homologue, the antagonist and 23 nM $^3$H-thymidine were added. After an additional 48 hours, the cell monolayer was washed twice with PBS, and the cells were then removed with 1 ml 10×trypsin containing 5 mM EDTA. The cells were harvested with a Skatron filter apparatus, and the filters counted in a scintillation counter.

Procedure D

Stimulation of Ca$^{2+}$Release in SCLC

Following the procedure of Heikkila et al., J Biol. Chem. 262 16456 (1987), approximately 1×10$^8$ H345 SCLC cells, maintained in RPMI-1640 (Ro) medium supplemented with selenium, insulin, and transferrin, were harvested by settling and washed with Ro. They were then resuspended in 2 ml Ro, to which 1.2 nmol Fura-2/AM per 10$^6$ cells was added. After a 15 minute incubation at 37° C., the cells were diluted to 10 ml with Ro and incubated for 1 hour at 37° C., the cells were then centrifuged and resuspended in HEPES-saline (140 mM NaCl, 5mM KCl, 5mM glucose, 1 mM CaCl$_2$, 1 mM MgCl$_2$, 20 mM HEPES, pH 7.4) at a density of 2.5-5×10$^6$cells/ml. The cells were kept on ice for up to 2 hours before being used. Ca$^{2+}$measurements were performed at 37° C. in an Aminco SPF-500 fluorimeter. The excitation wavelength was 340 nm, the emission wavelength 510 nm. Two ml of cell suspension was periodically resuspended in a 3 ml plastic cuvette. They were equilibrated at 37° for at least 5 minutes data was collected. After a stable baseline was established, the compound of interest was added, and data was collected for approximately 5 minutes. At that time, a challenge dose of GRP 14–27 was added, and data was collected for an additional 5 minutes. The cells were then lysed with 4 μl 10% Triton X-100 to measure peak fluorescence. Baseline fluorescence was measured after the subsequent addition of 40 μl 2M tris (pH 9.5) and 64 μl 0.2M EGTA.

The following results were obtained with the antagonist identified in Example 1:

Procedure A: The antagonist blocks binding of the radioligand with an IC$_{50}$ of approximately 5 nM.

Procedure B: The antagonist does not stimulate mitogenesis at concentrations up to 10 mM.

Procedure C: The antagonist blocks mitogenic stimulation of 3 nM human GRP with an IC$_{50}$ of approximately 20 nM.

Procedure D: The antagonist blocks the Ca$^{2+}$response elicited by 100 nM GRP14-27 with an IC$_{50}$ of approximately 300 nM.

The following examples illustrate the present invention without, however, limiting the same thereto. Unless indicated otherwise, all optically active amino acids have L configuration.

EXAMPLE 1

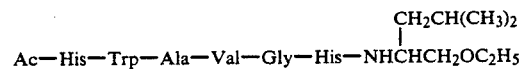

Ac—His—Trp—Ala—Val—Gly—His—NHCHCH$_2$OC$_2$H$_5$

Step 1. Preparation of Ac-His-Trp-Ala-Val-Gly

This peptide was prepared by a standard solid phase procedure beginning with BOC-glycyl resin with additional amino acids added with DCC coupling.

Step 2. (S)-1-Ethoxy-2-amino-4-methylpentane (S)-leucinol (6.4 mL, 5 mmol) was added over 30 minutes to a well stirred slurry of 6% sodium hydride (2.2 g, 55 mmol) in THF (50 mL) at room temperature under N$_2$. After all of the sodium hydride had reacted, a solution of ethyl iodide (4 mL, 50 mmol) in THF (50 mL) was added and the reaction stirred at 20°-25° C. for 20 hours. THF was removed under reduced pressure and the residue partitioned between diethyl ether and brine. The ether extract was dried (Na$_2$SO$_4$), filtered and concentrated under reduced pressure. The residue was flash chromatographed over silica gel and pure aminoether eluted with a mixture of 10% isopropanol and 90% chloroform.

Step 3. N-[(S)-1-Ethoxy-4-methyl-2-pentyl] N$_\alpha$-N$_{im}$-Bis-Boc-(S)-Histidineamide A mixture of N$_\alpha$-N$_{im}$-bis-BOC-histidine ethyl acetate solvale (1.92 g, 5.0 mmol), 4-methylmorpholine (0.55 mL, 5.0 mmol) and isobutyl chloroformate (0.65 mL, 5.0 mmol) in ethyl acetate (50 mL) was stirred in an ice bath under N$_2$ for 15 minutes. A solution of (S)-1-ethoxy-2-amino-4-methylpentane (0.73 g, 5.0 mmol) in ethyl acetate (2 mL) was then added and the reaction stirred at room temperature for 20 hours. After washing with 10% citric acid, brine, saturated NaHCO$_3$ solution and brine, the ethyl acetate extract was dried (Na$_2$SO$_4$), filtered and concentrated under reduced pressure. The residue was flash chromatographed over silica gel. Elution with a mixture of 2% methanol and 98% chloroform afforded pure BOC-protected histidineamide (0.90 g).

Step 4. N-[(S)-1-Ethoxy-4-methyl-2-pentyl](S)-Histidine-amide

A solution of the BOC-protected amide from step 3 (0.90 g) in ethyl acetate (25 mL) was cooled in an ice bath and saturated with HCl gas for 5 minutes. After stirring at ice bath temperature for 1 hour, solvent was removed under reduced pressure and the residue dried to give the deprotected amide hydrogen chloride salt (0.67 g).

Step 5.

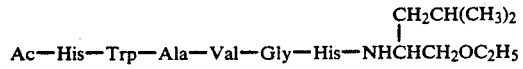

Step 5. Ac-His-Trp-Ala-Val-Gly-His-NHCHCH₂OCH₅

A solution of the histidine amide hydrogen chloride salt from Step 4 (16 mg), the peptide of Step 1 (23 mg), 1-hydroxybenzotriazole (5.4 mg), triethylamine (14 μL) and dicyclohexylcarbodiimide (7.2 mg) in DMF (3 mL) was stirred at room temperature under $N_2$ for 20 hours. After concentrating under reduced pressure, the residue was mixed with distilled water and filtered. The aqueous extract was washed with ethyl acetate two times, filtered and lyophilized to give a white powder. This product was purified by preparative HPLC to give the product as a white solid, homogeneous TLC (silica gel eluted with a mixture of 20% methanol and 80% chloroform, saturated with $NH_3$), 97.5% pure by reverse-phase HPLC (95% pH 2.4 $H_3PO_4$—5% $CH_3CN$ to 60% pH 2.4 $H_3PO_4$—40% $CH_3CN$ gradient).

EXAMPLE 2

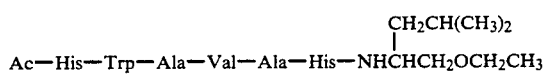

This compound is obtained by substituting alanine for glycine in Step 1 of Example 1.

EXAMPLES 3-11

The compounds of the foregoing formula wherein R is the entity in Column 1 are obtained by substituting the compound in Column 2 for $C_2H_5I$ in Step 2 of Example 1.

| Example | Column 1 | Column 2 |
|---|---|---|
| 3 | CH₃ | CH₃I |
| 4 | CH(CH₃)₂ | (CH₃)₂CHI |
| 5 | CH₂(CH₂)₄CH₃ | CH₃(CH₂)₅I |
| 6 | 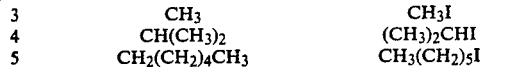 | |
| 7 | 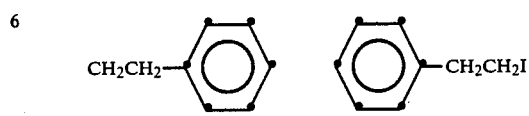 | |
| 8 | 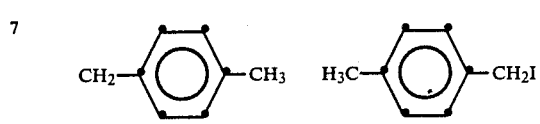 | |
| 9 | CH₂CH₂CH₂F | FCH₂CH₂CH₂I |
| 10 | CH₂CH₂CH₂Cl | ClCH₂CH₂CH₂I |
| 11 | CH₂CH₂CH₂CF₃ | F₃CCH₂CH₂CH₂I |

EXAMPLES 12-16

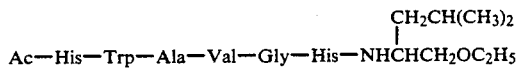

Compounds of the foregoing formula wherein one amino acid is substituted by a D-amino acid are obtained by following the procedure of Example 1 but substituting the following peptide for that in Step 1.

| Example | Peptide |
|---|---|
| 12. | Ac—D—His—Trp—Ala—Val—Gly |
| 13. | Ac—His—D—Trp—Ala—Val—Gly |
| 14. | Ac—His—Trp—D—Ala—Val—Gly |
| 15. | Ac—His—Trp—Ala—D—Val—Gly |
| 16. | Ac—His—Trp—Ala—Val—D—Ala |

EXAMPLE 17

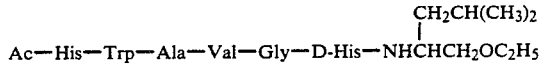

The title compound is obtained by following the procedure of Example 1 but substituting di-BOC-D-Histidine for di-BOC-L-histidine in Step 3.

EXAMPLE 18

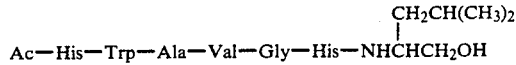

The title compound is obtained following the procedure of Example 1 but substituting (S)-leucinol for (S)-1-ethoxy-2-amino-4-methyl pentane in step 3.

EXAMPLE 19

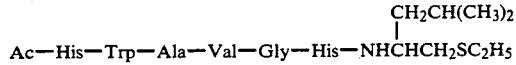

Step 1 (S)-2-Amino-1-ethylthio-4-methylpentane (S)-2-Amino-4-methyl-1-pentanethiol (6.66 g, 50 mmol) is added over 45 minutes to a well stirred slurry of 60% sodium hydride (2.0 g, 50 mmol) in THF (50 mL) at room temperature under $N_2$. After all of the sodium hydride has reacted, a solution of ethyl iodide (4 mL, 50 mmol) in THF (50 mL) is added and the reaction stirred at 20°-25° C. for 18 hours. THF is removed under reduced pressure and the residue partitioned between diethylether and brine. The ether extract is dried (Na2SO4), filtered and concentrated under reduced pressure. Flash chromatograp

Step 2. N-[(S)-1-Ethylthio-4-methyl-2-pentyl]-Nα, Nim-bis BOC-(S)-histidineamide.

A mixture of NαNim-bis BOC-(S)-histidine ethyl acetate solvate (0.96 g, 2.50 mmol), 4 methyl-morpholine (0.28 mL, 2.50 mmol) and isobutyl chloroformate (0.33 mL, 2.50 mmol) in ethyl acetate (35 mL) is stirred in an ice bath under N2 for 15 minutes. A solution of (S)-2-amino-1-ethylthio-4-methyl pentane (0.40 g, 2.50 mmol) in ethyl acetate (2 mL) is then added and the reaction stirred at room temperature for 18 hours. After washing with 10% citric acid, brine, saturated NaHCO3 solution and brine, the ethyl acetate extract is dried (Na2SO4), filtered and concentrated under reduced pressure. The residue is flash chromatographed over silica gel. Elution with a mixture of 2% methanol- 98% chloroform affords pure BOC-protected histidineamide.

Step 3. N-[(S)-1-Ethylthio-4-methyl-2-pentyl]-(S)-histidineamide Hydrochloride.

A solution of the BOC-protected amide from Step 2 (0.75 g) in ethyl acetate (25 mL) is cooled in an ice bath and saturated with HCl gas for 5 minutes. After stirring at ice bath temperature for 40 minutes, solvent is removed under reduced pressure and the residue dried to give the deprotected amide HCl salt.

Step 4.

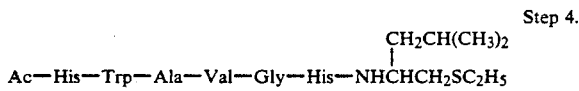

A solution of the histidine amide HCl salt from Step 3 (29.8 mg, 100 μmol), the peptide of Example 1, Step 1 (37.2 mg, 50 μmol), 1-hydroxy-benzotriazole hydrate (10.7 mg), triethylamine (35 μL, 250 μmol) and dicyclohexylcarbodiimide (20.7 mg, 100 μmol) in DMF (8 mL) is stirred at room temperature under N2 for 20 hours. After concentrating under reduced pressure, the residue is mixed with distilled water and filtered. The aqueous extract was washed two times with ethyl acetate, filtered and lyophilized to give a white powder. This crude product is purified by preparative HPLC to give pure peptide.

EXAMPLE 20

After filtering, solvent is removed under reduced pressure to give the propylamino derivative as an oil.

Step 2. (S)-N-Propyl-N-[2-(N-tert.butoxycarbonyl-amino)4-methylpentyl]-benzylcarbamate.

A solution of carbobenzyloxychloride (1 70 g, 10 mmol) in THF (15 mL) is added slowly to a stirred, cooled solution of the amine from Step 1 (2.58 g, 10 mmol) and diisopropyl ethylamine (1.29 g, 10 mmol) in THF (50 mL). After stirring at room temperature overnight, solvent is removed under reduced pressure and the residue partitioned between ethyl acetate and water. The ethyl acetate solution is washed with 10% citric acid, saturated sodium bicarbonate solution and brine. After drying (Na2SO4) and filtering, ethyl acetate is removed under reduced pressure to give the CBZ and BOC protected diamine.

Step 3. (S)-N-Propyl-N-(2-amino-4-methylpentyl)-benzylcarbamate Hydrochloride A solution of the BOC-protected amine from Step 2 (1.0 g) in ethyl acetate (30 mL) is cooled in ice bath and saturated with HCl gas for 5 minutes. After stirring at ice bath temperature for 40 minutes, solvent is removed under reduced pressure and the residue dried to give the amine hydrochloride salt.

Step 4. N-[(S)-1-(N-Propyl-N-benzyloxycarbonylamino)-4-methyl-2-pentyl]-Nα, Nim-bis BOC-(S)-histineamide A mixture of Nα-Nim-bis BOC-(S)-histidine ethyl acetate solvate (0.77 g, 2.0 mmol), 4-methyl-morpholine (0.22 mL, 2.0 mmol) and isobutyl chloroformate (0.26 mL, 2.0 mmol) in ethyl acetate (50 mL) is stirred in an ice bath under N2 for 15 minutes. (S)-N-Propyl-N-(2-amino-4-methylpentyl)-benzylcarbamate (0.58 g, 2.0 mmol) dissolved in ethyl acetate (5 mL) is then added and the reaction mixture stirred at room temperature for 24 hours. After washing with 10% citric acid, brine, saturated NaHCO3 solution and brine, the ethyl acetate extract is dried (Na2SO4), filtered and concentrated under reduced pressure. The residue is flash chromatographed over silica gel and product eluted with a mixture of 2–10% methanol chloroform.

Step 5. N-[(S)-1-(N-Propyl-N-benzyloxycarbonylamino)-4-methyl-2-pentyl]-(S)-histidineamide

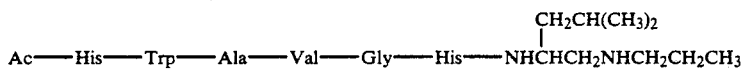

A solution of the BOC protected amide form Step 4 (0.50 g) in ethyl acetate (15 mL) is cooled in an ice bath and saturated with HCl gas for 5 minutes. After stirring at ice bath temperature for 1 hour, solvent is removed under reduced pressure and the residue dried to give the deprotected HCl salt.

Step 1. (S)-N-Propyl-N-[2-N-tert.butoxycarbonylamino)-4-methylpentyl]amine.

Propylamine (2.96 g, 50 mmol) is added to a solution of BOC-(S)-leucinal (10.76 g, 50 mmol) in ethanol (100 mL) and the solution hydrogenated in a Paar apparatus with 5% palladium on carbon as catalyst at an initial pressure of 38 psi until hydrogen uptake is complete.

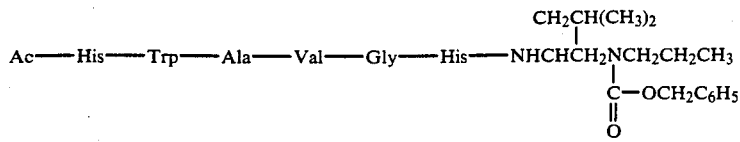
Step 6.

A solution of the histidine amide form Step 5 (50 mg), the peptide of Example 1, Step 1 (37.2 mg), 1-hydroxybenzotriazole (10.7 mg), triethylamine (35 μL) and dicyclohexylcarbodiimide (21 mg) in DMF (10 mL) is stirred at room temperature under $N_2$ for 20 hours. After concentrating under reduced pressure, the residue is mixed with distilled water and filtered. The aqueous extract is washed with ethyl ether, filtered lyophilized. The residue is purified by preparative HPLC to give pure peptide.

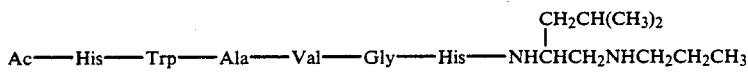
Step 7.

A solution of 20 mg of the peptide from Step 6 in water (10 mL) and methanol (5 mL) is hydrogenated over a 5% palladium on carbon catalyst in a pressurized vessel at an initial pressure of 20 psi for 2 hours. After filtering, solvents are removed under reduced pressure. The residue is purified by preparative HPLC to give pure deprotected peptide.

What is claimed is:
1. A compound of the formula

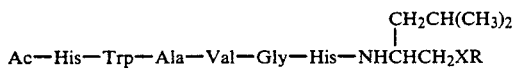

wherein Ac is acetyl, X is 0, S or N—H, R is hydrogen or an alkyl radical of 1-6 carbon atoms, or an alkyl radical of 1-6 carbon atoms containing an aromatic radical in which optically active carbon atoms are in the S configuration, wherein both the alkyl and aromatic radicals are substituted with alkyl of from 1 to 3 carbon atoms, hydroxy, alkoxy of from 1 to 3 carbon atoms, halogen, trifluoromethyl and wherein any one optically active amino acid may be substituted by its D-isomer, and glycine may be substituted by Ala or D-Ala.

2. A compound of claim 1 wherein X is 0.
3. A compound of claim 1 wherein X is S.
4. A compound of claim 1 wherein X is N—H.
5. A compound of claim 1 wherein X is 0 and R is $C_2H_5$.
6. A compound of the formula Ac—His—Trp—Ala—Val—Gly—His—NHCHCH$_2$XR
                                               |
                                          CH$_2$CH(CH$_3$)$_2$ wherein Ac is acetyl, X is 0, S or N—H, R is hydrogen or an alkyl radical of 1-6 carbon atoms, or an alkyl radical of 1-6 carbon atoms containing an aromatic radical in which optically active carbon atoms are in the S configuration.

7. A compound of claim 6 wherein X is 0.
8. A compound of claim 6 wherein X is S.
9. A compound of claim 6 wherein X is N—H.
10. A compound of claim 6 wherein X is 0 and R is $C_2H_5$.

* * * * *